(12) United States Patent
Dohi et al.

(10) Patent No.: US 6,835,389 B1
(45) Date of Patent: Dec. 28, 2004

(54) POWDER COMPOSITION FOR NASAL ADMINISTRATION

(75) Inventors: Masahiko Dohi, Hino (JP); Yasuhide Uejima, Hino (JP); Takao Fujii, Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/763,671

(22) PCT Filed: Aug. 24, 1999

(86) PCT No.: PCT/JP99/04559

§ 371 (c)(1),
(2), (4) Date: Feb. 26, 2001

(87) PCT Pub. No.: WO00/12063

PCT Pub. Date: Mar. 9, 2000

(30) Foreign Application Priority Data

Aug. 26, 1998 (JP) .......................................... 10/240241
Sep. 16, 1998 (JP) .......................................... 10/261687

(51) Int. Cl.[7] .............................. A61F 13/02; A61K 9/50
(52) U.S. Cl. ........................ 424/434; 424/499; 424/501
(58) Field of Search ................................ 424/434, 499, 424/501

(56) References Cited

U.S. PATENT DOCUMENTS 6,428,805 B1    8/2002  Dohi et al.

FOREIGN PATENT DOCUMENTS

| EP | 06 06 486 A | 7/1994 |
| JP | 6-504539 | 5/1994 |
| JP | 9-291025 | 11/1997 |
| JP | 10-59841 | * 3/1998 |
| JP | 10-114645 | 5/1998 |
| WO | WO 91 06282 A | 5/1991 |

OTHER PUBLICATIONS

Abstract 10059841 Mar. 03, 1998.
Abstract 09291025 Nov. 11, 1997.
Abstract 10114645 May 06, 1998.

* cited by examiner

*Primary Examiner*—Carlos A. Azpuru
(74) *Attorney, Agent, or Firm*—Sughrue Mion, PLLC

(57) ABSTRACT

There is provided a powder composition for nasal administration comprising a drug having a particle size of less than 10 μm or a lyophilized drug, a water-absorbing and water-slightly soluble base material, and a water-absorbing and gel-forming base materials. The composition has excellent drug absorbability.

18 Claims, No Drawings

POWDER COMPOSITION FOR NASAL ADMINISTRATION

FIELD OF THE INVENTION

The present invention relates to powder compositions for nasal administration having an improved drug absorbability via nasal mucosa. More specifically, the present invention relates to powder compositions for nasal administration that exhibit high maximum blood concentration by using a drug having a specific particle size or a lyophilized drug, and a base material of a specific type or composition.

DESCRIPTION OF THE RELATED ART

Because, in non-peptide/protein drugs such as anti-inflammatory steroids, (1) local nasal mucosa can be a target as an active size, (2) an immediate action may be desired, and (3) some have low absorbability via oral administration, and the like, there has been a need for the development of drugs for nasal administration.

Many peptide/protein drugs are not readily absorbed into the body because, when orally administered, they tend to be decomposed by proteolytic enzymes in the gastrointestinal tract. Therefore, injection has to be used for therapeutic uses of these drugs in many cases. However, injections impose a heavy burden on patients because of pain, the need for hospital visits etc. Thus, there is a strong need, for these drugs, for the development of noninvasive administration regimen that can replace injections.

Nasal administration is a method of administration in which drugs are transported through the nasal mucosa into the blood circulation. Nasal administration is under intensive research as a non-injection type administration together with, for example, subcutaneous, ocular, rectal, and pulmonary administration and the like. Among the non-injection type administrations, nasal administration is easy to perform. In addition, since the blood system is more developed in the nasal mucosa compared to the skin, the ocular mucosa, the rectal mucosa, and the like, the nasal administration is thought to have excellent absorbability among the non-injection type administrations. Formulations for nasal administration have indeed been put into practice for some drugs. Furthermore, since, in nasal administration, drugs migrate into the blood more rapidly than in oral administration, immediate action almost equal to injections can be expected for nasal administration. However, the absorption of drugs thought nasal mucosa depends on the physical properties such as lipophilicity, molecular weight, and the like. It has been postulated that highly water-soluble drugs, highly lipophilic drugs, peptide/protein drugs having high molecular weight etc. generally have low absorbability. Thus, various methods are postulated to enhance absorbability of drugs through nasal mucosa.

For example, Japanese Examined Patent Publication (Kokoku) No. 60-34925 reports on a prolonged-action formulation for the nasal cavity comprising a cellulose ether and a drug.

Prolonged-action formulations for nasal cavity described in the above publication are formulations intended to adhere to the nasal mucosa and to gradually release the drug, and thereby it is possible to allow the drug to be absorbed via the nasal mucosa to effect prolonged release of the effective amount of the drug. However, since the prolonged-action formulation for nasal cavity described in said publication points to sustained release of the drug, enough ability has not been given, it is believed, to the function of promoting the absorption of the drug. Drugs exemplified in the preferred embodiment are anti-inflammatory steroids, analgesic anti-inflammatory drugs, anti-histaminics, and drugs having anti-allergic actions and the like, for which the maintenance of local drug concentration is more important than absorbability into the systemic blood circulation.

Thus, in the prolonged-action formulations described in the above publication, a high nasal absorbability could not be expected for highly water-soluble drugs, highly lipophilic drugs, and high molecular weight peptide/protein drugs. Thus, there is a strong need for the development of compositions for administration via the nasal mucosa that can be effectively utilized in terms of therapeutic effects and therapeutic efficiency.

Nolte et al. (Hormone Metabolic Research Vol. 22, 170–174, 1991) and Bruice et al. (Diabetic Medicine Vol. 8, 366–370, 1991) reported on insulin formulations for nasal administration that contained an absorption promoter for sodium glycolate or taurofusidic acid sodium. These absorption promoters, however, have a problem of irritating nasal mucosa, and have not been put into practical use.

On the other hand, Japanese Examined Patent Publication (Kokoku) No. 62-42888 reported on powder compositions for nasal administration having an excellent absorbability via the nasal mucosa, said compositions comprising polypeptides and a water-absorbing and water-slightly soluble base material. It is also reported that such compositions permit the nasal absorption of polypeptides without using such an absorption promoter.

However, even in the compositions of the above publication, the nasal absorption rate of polypeptides (the area under the blood concentration versus time curve (AUC) after nasal administration) does not exceed 10 to 20% of that after the injection administration. For example, according to Example 4 in the publication, the maximum blood concentration after administration of 10 units of insulin to rabbits in 200 µU/ml or less, or about 20% of that of the injection administration, and the absorption rate calculated from the AUC is estimated to be not greater than 10%.

The publication also describes a combined use of a water-absorbing and water-readily soluble base material and a water-absorbing and water-slightly soluble base material at a ratio of 0.1 to 60% by weight, most preferably 0.1 to 50% by weight relative to the water-absorbing and water-slightly soluble base material.

However, the publication only states that the objective or effect of such a combined use in sustained-release effects (sustained-release or prolonged action) compared to when a water-absorbing and water-slightly soluble base material is used alone.

Furthermore, the publication makes no mention of using non-peptide/protein drugs instead of polypeptides.

Furthermore, the publication illustrates, by way of example, many water-absorbing and water-slightly soluble base materials including crystalline cellulose and many water-absorbing and water-readily soluble base materials including hydroxypropyl cellulose. The publication, however, makes no mention that certain combinations of specific types, compositions, and particle sizes of these base materials can provide powder compositions for nasal administration that exhibit excellent maximum blood concentrations for peptide/protein drugs and non-peptide/protein drugs.

Furthermore, said publication states that it is important that 90% by weight or more of the particles of the composition have a particle size of 10 to 250 µm to attain good absorbability and that the drug (limited to polypeptides therein) and the base material can be present separately considering the state of the composition and the method of preparation. It is clear, in this case, that the particle size of the drug is not less than 10 µm. The publication does not make any mention either that particle size of less than 10 µm can lead to powder compositions for nasal administration having further excellent maximum blood concentrations.

The publication also suggests that lyophilized polypeptides may be used. However, it is a common knowledge among those skilled in the art that many of polypeptides should be lyophilized when they are present as solids because of their physical properties including stability. The publication makes no mention of using non-peptide/protein drugs that, in the lyophilized form, generally exhibit better stability compared to polypeptides, much less of using them to enhance maximum blood concentrations after the nasal administration thereof.

Japanese Unexamined Patent Publication (Kokai) No. 10-114645 describes powder formulations for nasal administration comprising powders of absorptive resins and active peptides, and refers to the use of active peptides having a particle size of 10 µm or less. The particle size was selected in order to improve the absorption of active peptides to adsorptive resins. The publication makes no mention of using, in combination, two types of base materials of the present invention at certain ratios, or of the fact that the combined use can lead to enhanced absorbability.

Peptide/protein drugs are generally expensive, and in many cases the poor absorbability thereof leads to large variation in blood concentrations, and thereby to failure in obtaining the desired therapeutic effects on a continual basis. Thus, there is a need for compositions of peptide/protein drugs for nasal administration that exhibit higher absorbability. There is also a strong need for compositions for nasal administration that are more stable and exhibit better absorbability. There is also a need for compositions for nasal administration that are capable of providing enhanced maximum blood concentrations. This holds true for non-peptide/protein drugs as well.

BRIEF SUMMARY OF THE INVENTION

As hereinbefore stated, though the nasal administration of drugs have various advantages as an administration regimen, there remains much to be desired in terms of absorbability, maximum blood concentrations and the like.

It is an object of the present invention to provide compositions for nasal administration that exhibit excellent absorbability of drugs.

It is also an object of the present invention to provide compositions for nasal administration that exhibit excellent absorbability of drugs and, among others, higher maximum blood concentrations.

It is a further object of the present invention to provide compositions for nasal administration that exhibit excellent absorbability and, among others, higher maximum blood concentrations even for highly water-soluble drugs, highly lipophilic drugs, and high molecular weight peptide/protein drugs.

It is also an object of the present invention to provide compositions for nasal administration that exhibit still better absorbability and, among others, higher maximum blood concentrations even for highly water-soluble drugs, highly lipophilic drugs, and non-peptide/protein drugs that originally have good nasal absorbability.

It is a further object of the present invention to provide safe compositions for nasal administration.

After intensive research to solve the above problems, the inventors of the present invention have found that by using drugs having specific particle sizes or lyophilized drugs and base materials of specific types or compositions, it is possible to provide novel powder compositions for nasal administration that exhibit excellent absorbability even for drugs that have low absorbability via the nasal mucosa and non-peptide/protein drugs, and novel powder compositions for nasal administration that exhibit markedly high maximum blood concentrations, and thereby have attained the present invention.

Thus, the present invention provides a powder composition for nasal administration comprising (1) a drug having a particle size of less than 10 µm, (2) a water-absorbing and water-slightly soluble base material, and (3) a water-absorbing and gel-forming base material.

The present invention also provides powder compositions for nasal administration comprising (1) a lyophilized drug, (2) a water-slightly soluble and water-absorbing base material, and (3) a water-absorbing and gel-forming base material.

DETAILED DESCRIPTION OF THE INVENTION

As the drugs of the present invention, there can be preferably mentioned non-peptide/protein drugs and peptide/protein drugs.

As the non-peptide/protein drugs of the present invention, there are available a wide variety of non-peptide/protein drugs. Specific examples thereof include anti-inflammatory steroids or non-steroidal anti-inflammatory agents, analgesic anti-inflammatory agents, sedatives, anti-depressants, antitussive expectorants, antihistamics, anti-allergy agents, antiemetics, hypnotics, vitamins, sex steroid hormones, anticancer agents, antiarrhythimics, antihypertensives, antianxiety drugs, psychotropic agents, anti-ulcer agents, cardiotonics, analgesics, bronchodilators, anti-obesity agents, anti-platelet aggregation agents, anti-diabetics, muscle relaxants, anti-migraine agents, antirheumatics, and the like. As the non-peptide/protein drugs, one or more than one selected from the group consisting of the above can be used. Among others, one or more than one selected from the group consisting of antiemetics, hypnotics, vitamins, sex steroid hormones, anti-migraine agents, and analgesics may be mentioned as preferred examples.

As the non-peptide/protein drugs, there can be mentioned one or more than one non-peptide/protein drug selected from the group consisting of anti-inflammatory steroids or non-steroidal anti-inflammatory agents such as hydrocortisone, prednisolone, triamcinolone, dexamethasone, betamethasone, beclometasone, fluticasone, mometasone, fluocortine, budesonide, salbutamol, and salmaterol; analgesic anti-inflammatory agents such as acetaminophen, phenacetin, aspirin, aminopyrine, sulpyrine, phenylbutasone, mefenamic acid, flufenamic acid, ibuprofen, alclofenac, dichlofenac, and indomethacin; sedatives such as scopolamine; anti-depressants such as imipramine; antitussive expectorants such as sodium cromoglycate, codeine phosphate, and isoproternol hydrochloride; antihistamics such as diphenhydramine, triprolidine, isothipendyl, and chlorpheniramine; anti-allergy agents such as anlexanox, azelastin, ozagrel, tranilast, and ketotifen; antiemetics such as ondansetron, granisetron, metoclopramide, cisapride, and domperidone; hypnotics such as brotizolam and melatonin; vitamins such as cyanocobalamin and mecobalamin; sex steroid hormones such as estradiol, estriol, progesterone, and testosterone; anti-cancer agents such as tamoxifen and tegafur; antiarrhthmics such as proplanolol and atenolol; antihypertensives such as nicardipine; antianxiety drugs such as diazepam; psychotropic agents such as nitrazepam; anti-ulcer agents such as cimetidine and ranitidine; cardiotonics such as dopamine; analgesics such as morphine and buprenobhine; bronchodilators such as oxitropium and ozagrel; anti-obesity agents such as madindol; anti-platelet aggregation agents such as beraprost and carbacyclin; anti-diabetics such as acarbose and sorbinil; muscle relaxants such as pinaverium and inaperisone; anti-migraine agents such as ergotamine, imigran and alniditan; antirtheumatics such as actarit and platonin, and the like.

As the peptide-protein drugs of the present invention, those having a molecular weight of 30,000 or smaller are preferred. As the peptide/protein drugs with a molecular weight of 30,000 or smaller, there can be mentioned luteinizing hormone releasing hormones, growth hormone releasing factors, somatostatin derivatives, vasopressins, oxytocins, hirudine derivatives, enkephalins, adrenocorticotropic hormone derivatives, bradykinin derivatives, calcitonins, insulins, glucagon derivatives, growth hormones, growth hormone releasing hormones, luteinizing hormones, insulin-like growth factors, calcitonin gene-related peptides, atrial natriuretic peptide derivatives, interferons, interleukins, erythropoietin, granulocyte colony-stimulating factor. macrophage forming stimulating factor, parathyroid hormones, parathyroid hormone releasing hormones, prolactin, thyroid stimulation hormone releasing hormone, angiotensins, and the like. As the peptide/protein drugs of the present invention, there can be used one or more than one selected from the group consisting of these specific examples.

In one aspect of the present invention, the particle size of the drugs is less than 10 μm. However, too finely-divided particles, though absorption-promoting effects may be observed, have drawbacks that their scattering nature makes pharmaceutical handling difficult, and thereby the preferred particle size is 0.5 μm or more and less than 10 μm.

As a method of adjusting the particle size of drugs to 10 μm, there can be mentioned methods using the pressing-type pulverization such as with a mortar, the rotating collision-type pulverization such as with centrifugation, and, in addition, methods using a spray drier, and a freeze drier, and the like.

In another aspect of the present invention, lyophilized drugs may be used. As a method of lyophilizing drugs of the present invention, there can be mentioned the method of merely dissolving drugs in an aqueous medium such as purified water followed by lyophilization, and, when the solubility of the drug is low, the method of adjusting pH of the drug with an additive or adding a solubilizer to the drug followed by lyophilization. Conditions of lyophilization in these cases are preferably (1) the concentration of the drug solution to be lyophilized is in the range from its saturated solubility in the solvent at room temperature to ⅕ thereof, (2) the drug solution is cooled and frozen to −20° C. to −40° C. at a rate of 0.5° C./hr or higher, (3) depressurized to vacuum, (4) heated to 5° C. to 10° C. at a rate of 2.0° C./hr or lower, (5) increasing the time of primary drying to 6 to 10 hours while keeping the temperature at 5° C. to 10° C., (6) heating again to room temperature ±5° C., and (7) performing secondary drying. by satisfying these conditions, the effects of the present invention can be fully enhanced.

The base material of the present invention that is water-absorbing and gel-forming (hereinafter referred to as the gel-forming base material) is one or more than one selected from the group consisting of hydroxypropyl cellulose, hydroxypropyl methyl cellulose, methyl cellulose, hydroxy ethyl cellulose, and carboxymethyl cellulose sodium.

Among them, preferred gel-forming base materials of the present invention are one or more than one selected from the group consisting of hydroxypropyl cellulose, hydroxypropyl methyl cellulose, methyl cellulose, and carboxymethyl cellulose sodium, with hydroxypropyl cellulose being most preferred.

A preferred hydroxypropyl cellulose is one wherein a 2% aqueous solution has a viscosity of 150 to 4,000 cps. Viscosity as used herein means a kinematic viscosity, which is measured by viscometers such as the Cannon-Fenske viscometer, the Ubbelohde viscometer for the Cannon-Fenske opaque solution, and the Ostwald viscometer. Among them, measurement with the Ubbelohde viscometer is preferred because it is very precise. The viscosity values described in the present specification were determined using the Ubbelohde viscometer manufactured by Shibata Kagaku Kikai Kogaku at an environment of 37° C.

Some of the hydroxypropyl celluloses have lower viscosity than the above. But, when those with a viscosity of lower than 150 cps are used, the effect of enhancing maximum blood concentrations is not always satisfactory.

With regard to the gel-forming base materials constituting the composition of the present invention, it is preferred that 90% by weight or more of the particles thereof have an average particle size in the range of 10 to 350 μm, and it is more preferred that 90% by weight or more of the particles thereof have an average particle size in the range of 20 to 250 μm because they lead to enhanced absorbability and increased blood concentrations. More preferably, 90% by weight or more of the particles thereof have an average particle size in the range of 60 to 110 μm, and by limiting, in this way, the particle size of the gel-forming base materials constituting the compositions of the present invention, effects of the present invention can be further enhanced.

The water-absorbing and water-slightly soluble base materials of the present invention include water-absorbing and water-insoluble base materials (hereinafter referred to as the water-slightly soluble base materials), and the water-slightly soluble base materials are one or more than one base material selected from the group consisting of crystalline cellulose, α-cellulose cross-linked carboxymethyl cellulose sodium, cross-linked starch, gelatin, casein, gum tragacanth, polyvinylpyrrolidone, chitin, chitosan, dextrin, kaolin, silicon dioxide hydrate, colloidal silicon dioxide, light silica, synthetic aluminum silicate, synthetic hydrotalcite, titanium oxide, dry aluminum hydroxy gel, magnesium carbonate, calcium carbonate, precipitated calcium carbonate, bentonite, aluminium magnesium metasilicate, calcium lactate, calcium stearate, calcium hydrogen phosphate, phosphoric acid anhydride, calcium hydrogen, and talc.

Among them, preferred water-slightly soluble base materials of the present invention are one or more than one selected from the group consisting of crystalline cellulose, α-cellulose, cross-linked carboxymethyl cellulose sodium, cross-linked starch, gelatin, casein, gum tragacanth, chitin, chitosan, calcium hydrogen phosphate, calcium hydrogen, and precipitated calcium carbonate, with crystalline cellulose being most preferred.

With regard to the water-slightly soluble base materials constituting the composition of the present invention, it is preferred that 90% by weight or more of the particles thereof have an average particle size in the range of 10 to 350 μm, and it is more preferred that 90% by weight or more of the particles thereof have an average particle size in the range of 20 to 250 µm because they lead to enhanced absorbability and increased blood concentrations. More preferably, 90% by weight or more of the particles thereof have an average particle size in the range of 38 to 150 µm, and by limiting, in this way, the particle size of the water-slightly soluble base materials constituting the compositions of the present invention, effects of the present invention can be further enhanced.

As preferred combinations of the gel-forming base material and the water-slightly soluble base material of the present invention, there can be mentioned combinations of each of the above preferred examples. A particularly preferred combination is that of hydroxypropyl cellulose as the gel-forming base material and crystalline cellulose as the water-slightly soluble base material. In these cases, a particularly preferred example is such that 90% by weight or more of the particles have an average particle size in the range of 60 to 150 µm for the water-slightly soluble base material, and 90% by weight or more of the particles have an average particle size in the range of 38 to 110 µm for the gel-forming base material.

The relationship of the amounts of the gel-forming base material and the water-slightly soluble base material for use in the present invention is such that the mixed ratio by weight of said water-slightly soluble and water-absorbing base material to said gel-forming base material is in the range of 99:1 to 65:35, since they lead to high absorbability and high blood concentrations.

Since the amount of the gel-forming base material depends on the type of drugs of the present invention, the mixed ratio by weight of said water-slightly soluble and water-absorbing base material to said gel-forming base material is in the range of 90:10 to 65:35 in the case of non-peptide/protein drugs, since they lead to effects of enhancing maximum blood concentrations. When the drugs are peptide/protein drugs, preferred amounts of the gel-forming base material are further finely grouped depending on the molecular weight. When the molecular weight of peptide/protein drugs is 500 or more to less than 1,500, the mixed ratio by weight of said water-slightly soluble and water-absorbing base material to said gel-forming base material is preferably in the range of 95:5 to 70:30, since they lead to a marked effect of enhancing maximum blood concentrations. When the molecular weight of peptide/protein drugs is 1,500 or more to 30,000 or less, the mixed ratio by weight of said water-slightly soluble and water-absorbing base material to said gel-forming base material is preferably in the range of 95:5 to 80:20, since they lead to a marked effect of enhancing maximum blood concentrations.

Examples of the peptide/protein drugs having the above molecular weight of 500 or more to less than 1,500 include vasopressins, luteinizing hormones releasing hormones, growth hormone releasing hormones, somatostatin derivatives, oxytocins, hirudine derivatives, enkephalins, adrenocorticotropic hormone derivatives, and bradykinin derivatives. Examples of the peptide/protein drugs having the above molecular weight of 1,500 or more to 30,000 or less include calcitonins, insulins, glucagon derivatives, growth hormones, growth hormone releasing hormones, luteinizing hormones, insulin-like growth factors, calcitonin gel-related peptides, atrial natriuretic peptide derivatives, interferons, erythropoietin, granulocyte colony-stimulating factor, macrophage forming-stimulating factor, parathyroid hormones, parathyroid hormone releasing hormone, prolactin, thryoid stimulation hormone releasing hormone, and angiotensins.

The compositions of the present invention may be prepared by, for example, the following method.

According to one embodiment of the present invention, drugs having a particle size of less than 10 µm are mechanically mixed with water-slightly soluble base materials. On the other hand, according to a second embodiment, drugs are made aqueous solutions and lyophilized, and then the lyophilized drugs are mechanically mixed with water-slightly soluble base materials.

Subsequently, to mixtures obtained by either of the above first embodiment or the second embodiment, gel-forming base materials are mechanically mixed. As used herein, mechanical mixing refers to mixing with a fixed vessel-type mixer such as a high speed mixer and a rotary type mixer such as a V-shaped mixer. In particular, when water-slightly soluble base materials are mixed with drugs, mixing with a fixed-vessel type mixer is preferred since it markedly enhances the effects of the present invention. By using a fixed vessel-type mixer in the subsequent mixing with gel-forming base materials, the effects of the present invention are preferably markedly enhanced.

As used herein, the fixed vessel-type mixer includes universal mixers, ribbon mixers, automatic mortars, ball mills, and other mixers such as high speed mixers, fully automatic powered mixers, and manual press mixing with mortars. The rotary vessel-type mixer includes V-shaped mixers, cross rotary mixers, double cone-type mixers, and the like.

As the water-slightly soluble base materials and the gel-forming base materials of the present invention, there can be used microspheres having the above specific properties and comprising specific type of base materials such as starch and crystalline cellulose known as the base material for use in the powder compositions for nasal administration, as long as they satisfy the object of the present invention. In this case, it is preferred to use those having the particle size (for example 10 to 150 µm) that is similar to the particle size of the above water-slightly soluble base materials and the gel-forming base materials.

The amounts of the drug to be used in the present invention are therapeutically effective amounts, which may be determined by the type of the drug, and type and degree of the disease, the age and body weight of the patient, and the like. The amounts are generally 20 times, and more preferably an equal amount to 10 times that usually used for injection administration of the drug.

The amounts of the composition and the base material (the sum of the amounts of the water-slightly soluble base material and the gel-forming base material) of the present invention are limited in terms of the amounts of powder that can be applied to the nasal cavity, and the amounts are preferably similar to one weight of the drug, more preferably 5 weights or more per weight of the drug, and still more preferably 10 weights or more, though this cannot be conclusive because they depend on the amounts needed for treatment.

To the compositions of the present invention, there can be added, as desired, known lubricants, binders, diluents, colorants, preservatives, antiseptics, corrigents and the like, in order to improve physical properties as pharmaceutical drugs, appearances, smells, or the like. There can be mentioned talc, stearic acid and salts thereof, wax, etc., as lubricants; starch, dextran, etc., as binders; starch, lactose, etc., as diluents; red No. 2, etc., as colorants; ascrobic acid, etc., as preservatives; para-oxy benzoic acid esters, etc., as antiseptics; and menthol, etc., as corrigents.

The compositions of the present invention may be prepared in dosage forms suitable for administration as pharmaceutical formulations. Such forms include capsules in which unit doses of the compositions of the present invention have been filled, which are sprayed into the nasal cavity with a suitable dispenser.

Furthermore, unit doses or unit doses for several administrations of the composition of the present invention may be contained in a suitable device, and at the time of administration the unit doses of the compositions of the present invention may be given once or in several divided doses.

INDUSTRIAL APPLICABILITY

Thus, in accordance with the present invention, powder compositions for nasal administration that exhibit excellent nasal absorbability and a markedly enhanced maximum blood concentrations that conventional compositions for nasal administration are provided for highly water-soluble drugs, highly lipophilic drugs, and high molecular weight peptide/protein drugs.

Using the compositions of the present invention, it is possible to obtain markedly higher maximum blood concentrations at doses similar to the conventional drugs not only for expensive peptide/protein drugs but for non-peptide/protein drugs. Therefore, the amount of the drugs to be used can be reduced. Furthermore, it is possible to minimize variation in blood concentrations and thereby to obtain the desired therapeutic effects on a continual basis.

Furthermore, the compositions of the present invention have excellent absorbability (ability of maintaining blood concentrations) of drugs similarly to conventional powder compositions for nasal administration, and do not require the use of irritating absorption promoters, and thereby desired therapeutic effects are expected to be obtained on a continual basis.

Thus the present invention is extremely significant in medication that employs the administration of non-injection type drugs.

EXAMPLES

The present invention will now be explained with reference to Examples, which must not be construed to limit the present invention in any way.

In Examples that follow, crystalline cellulose may be described as microcrystalline cellulose and may sometimes be abbreviated as CC. Hydroxypropyl cellulose may sometimes be abbreviated as HPC.

Examples 1 to 2 and Comparative Examples 1 to 4

Buprenorphine hydrochloride (manufactured by Macfarlane Smith, Great Britain, average particle size of 65 μm) an analgesic, was ground on a mortar. To 4 mg of the drug ground to an average particle size of 5 μm added 180 mg or 160 mg of microcrystalline cellulose (manufactured by Asahi Chemical Industry, Co., Ltd.: Avicel PH101) and mixed in a mortar, to which 20 mg or 40 mg of hydroxypropyl cellulose (manufactured by Nippon Soda Co., Ltd.: HPC-H) and, as a lubricant, 0.16 mg of magnesium stearate were added and mixed in a mortar to prepare powder compositions (Examples 1 to 2).

For comparison, buprenorphine hydrochloride (manufactured by Macfarlane Smith, Great Britain, average particle size of 65 μm) was ground on a mortar. To 4 mg of the drug ground to an average particle size of 5 μm was added 110 mg or 80 mg of microcrystalline cellulose (manufactured by Asahi Chemical Industry, Co., Ltd.: Avicel PH101) and mixed in a mortar, to which 90 mg or 120 mg of hydroxypropyl cellulose (manufactured by Nippon Soda Co., Ltd.: HPC-H) and, as a lubricant, 0.16 mg of magnesium stearate were added and mixed in a mortar to prepare powder compositions (Comparative Examples 1 to 2).

Furthermore, for comparison, 4 mg of buprenorphine hydrochloride (manufactured by Macfarlane Smith, Great Britain, average particle size of 65 μm) was taken as it is. To the drug was added 180 mg or 160 mg of microcrystalline cellulose (manufactured by Asahi Chemical Industry, Co., Ltd.: Avicel PH101) and mixed in a mortar, to which 20 mg or 40 mg of hydroxypropyl cellulose (manufactured by Nippon Soda Co., Ltd.: HPC-H) and, as a lubricant, 0.16 mg of magnesium stearate were added and mixed in the mortar to prepare powder compositions (Comparative Examples 3 to 4).

In these cases, there were used microcrystalline cellulose (manufactured by Asahi Chemical Industry, Co., Ltd.: Avicel PH101) in which 90% by weight or more of the particles was made to have an average size of 63 to 150 μm, and hydroxypropyl cellulose (manufactured by Nippon Soda Co., Ltd.: HPC-H) in which 90% by weight or more of the particles have an average diameter of 10–100 μm.

These compositions were administered to the nasal cavity by Japanese white rabbits, weighing 2.5–3.0 kg, at a dose of 8 mg/kg using a pulverizer (manufactured by Teijin Ltd.: PUVRIZER). After a certain period of time, blood was taken from the ear vein, and blood concentrations of buprenorphine hydrochloride were measured by the HPLC method. The result is shown in Table 1.

When the particle size of buprenorphine hydrochloride is 10 μm or smaller and the mixed ratio by weight of the water-slightly soluble and water-absorbing base material CC to said gel-forming base material HPC is in the range of 99:1 to 65:35, higher maximum blood concentrations were observed than those observed when the mixed ratio of the water-slightly soluble and water-absorbing base material CC to said gel-forming base material HPC is 55:45 or 40:60 (Comparative Examples 1 to 2), indicating that the composition of the present invention exhibits markedly improved absorbability and markedly enhanced maximum blood concentrations.

TABLE 1

Changes with time in blood concentrations of buprenorphine hydrochloride after the administration of each composition (ng/ml)

| | CC | HPC | Particle size | 15 min. | 30 min. | 60 min. | 90 min. |
|---|---|---|---|---|---|---|---|
| Ex. 1 | 90 | 10 | 5 μm | 6.4 | 5.0 | 3.2 | 1.8 |
| Ex. 2 | 80 | 20 | 5 μm | 4.7 | 3.3 | 3.0 | 1.0 |
| Com. Ex. 1 | 55 | 45 | 5 μm | 1.0 | 1.2 | 0.8 | 0.6 |
| Com. Ex. 2 | 40 | 60 | 5 μm | 0.9 | 0.8 | 0.7 | 0.5 |
| Com. Ex. 3 | 90 | 10 | 65 μm | 0.5 | 1.0 | 0.4 | 0.2 |
| Com. Ex. 4 | 80 | 20 | 65 μm | 0.1 | 0.2 | 0.1 | 0 |

Note) In the table, CC and HPC represent weight ratios.

Examples 3 to 4 and Comparative Examples 5 to 8

To 20 mg of salmon calcitonin (manufactured by Mallinckrodt, USA, an average particle size of 2 μm), a peptide/protein drug, was added 19,000 mg or 18,000 mg of microcrystalline cellulose (manufactured by Asahi Chemical Industry, Co., Ltd.: Avicel PH101) and mixed in a high speed mixer. To the drug, 1,000 mg or 2,000 mg of hydroxypropyl cellulose (manufactured by Nippon Soda Co., Ltd.: HPC-H) and, as a lubricant, 16 mg of magnesium stearate were added and mixed in a cross rotary mixer to prepare powder compositions (Examples 3–4).

For comparison, to 20 mg of salmon calcitonin (manufactured by Mallinckrodt, USA, an average particle size or 2 μm) was added 10,000 mg or 8,000 mg of microcrystalline cellulose (manufactured by Asahi Chemical Industry, Co., Ltd.: Avicel PH101) and mixed in a high speed mixer. To the drug, 10,000 mg or 12,000 mg of hydroxypropyl cellulose (manufactured by Nippon Soda Co., Ltd.: HPC-H) and, as a lubricant, 16 mg of magnesium stearate were added and mixed in a cross rotary mixer to prepare powder compositions (Comparative Examples 5 to 6).

Furthermore, for comparison, salmon calcitonin (manufactured by Mallinckrodt, USA, an average particle size of 2 μm) was pressed and prepared to an average particle size of 15 μm. To the drug, 19,000 mg or 18,000 mg of microcrystalline cellulose (manufactured by Asahi Chemical Industry, Co., Ltd.: Avicel PH101) were added and mixed in a high speed mixer, and then 1,000 mg or 2,000 mg of hydroxypropyl cellulose (manufactured by Nippon Soda Co., Ltd.: HPC-H) and, as a lubricant, 16 mg of magnesium stearate were added and mixed in a cross rotary mixer to prepare powder compositions (Comparative Examples 7 to 8).

In these cases, there were used microcrystalline cellulose (manufactured by Asahi Chemical Industry, Co., Ltd.: Avicel PH101) in which 90% by weight or more of the particles was made to have an average size of 63 to 150 μm, and hydroxypropyl cellulose (manufactured by Nippon Soda Co., Ltd.: HPC-H) in which 90% by weight or more of the particles was made to have an average size of 10 to 100 μm.

These compositions were administered to the nasal cavity of Japanese white rabbits, weighing 2.5 to 3.0 kg, at a dose of 8 mg/kg using a pulverizer (manufactured by Teijin Ltd.: PUVRIZER). After a certain period of time, blood was taken from the ear vein, and blood concentrations of salmon calcitonin were measured by the RIA method. The result is shown in Table 2.

When the particle size of calcitonin is 10 μm or smaller and the mixed ratio by weight of the water-slightly soluble and water-absorbing base material CC to said gel-forming base material HPC is in the range of 99:1 to 65:35, higher maximum blood concentrations were observed than those observed when the mixed ratio of the water-slightly soluble and water-absorbing base material CC and said gel-forming base material HPC is 50:40 or 40:60 (Comparative Examples 5–6), indicating that the composition of the present invention exhibits markedly improved absorbability and markedly enhanced maximum blood concentrations.

TABLE 2

Changes with time in blood concentrations of salmon calcitonin after the administration of each composition (pg/ml)

| | CC | HPC | Particle size | 15 min. | 30 min. | 60 min. | 90 min. |
|---|---|---|---|---|---|---|---|
| Ex. 3 | 95 | 5 | 2 μm | 200 | 176 | 120 | 40 |
| Ex. 4 | 90 | 10 | 2 μm | 180 | 140 | 110 | 40 |
| Com. Ex. 5 | 50 | 50 | 2 μm | 45 | 25 | 20 | 20 |
| Com. Ex. 6 | 40 | 60 | 2 μm | 30 | 35 | 20 | 15 |
| Com. Ex. 7 | 95 | 5 | 15 μm | 100 | 80 | 65 | 40 |
| Com. Ex. 8 | 90 | 10 | 15 μm | 85 | 70 | 40 | 30 |

Note) In the table, CC and HPC represent weight ratios.

Reference Examples 1 to 6

Buprenorphine hydrochloride (manufactured by Macfarlane Smith, Great Britain, average particle size of 65 μm) was ground on a mortar and prepared to an average particle size of 20 μm or 5 μm. To 4 mg each of the non-ground drug and the drug ground to 20 μm or 5 μm was added 200 mg of lactose (manufactured by DMV: Pharmatose) and mixed in a mortar or not mixed. To the mixtures, 0.16 mg of magnesium stearate as a lubricant was further added and mixed in a mortar to prepare powder compositions.

These compositions were administered to the nasal cavity of Japanese white rabbits, weighing 2.5 to 3.0 kg, to a dose of buprenorphine hydrochloride+lactose at 1.6 mg/kg or 8 mg/kg using a pulverizer (manufactured by Teijin Ltd.: PUVRIZER). After a certain period of time, blood was taken from the ear vein, and blood concentrations of buprenorphine hydrochloride were measured by the HPLC method. The result is shown in Table 3.

It is clear that when buprenorphine hydrochloride alone or its mixture with lactose was administered to the nasal cavity, the particle size if buprenorphine hydrochloride does not significantly affect its absorbability, and the comparison of Examples 1 and 2 indicates that the composition of the present invention exhibits markedly improved absorbability and markedly enhanced maximum blood concentrations.

TABLE 3

Changes with time in blood concentrations of buprenorphine hydrochloride after the administration of each composition (ng/ml)

| Composition | | Dosage of BN | Particle size | 15 min. | 30 min. | 60 min. | 90 min. |
|---|---|---|---|---|---|---|---|
| Ref. Ex. 1 | BN alone | 1.6 mg/kg | 5 μm | 1.4 | 0.8 | 0.4 | 0 |
| Ref. Ex. 2 | BN alone | 1.6 mg/kg | 20 μm | 1.2 | 0.7 | 0.3 | 0 |
| Ref. Ex. 3 | BN alone | 1.6 mg/kg | 65 μm | 1.2 | 0.6 | 0.3 | 0 |
| Ref. Ex. 4 | BN + lactose + StMg | 0.16 mg/kg | 5 μm | 0.2 | 0 | 0 | 0 |
| Ref. Ex. 5 | BN + lactose + StMg | 0.16 mg/kg | 20 μm | 0.1 | 0 | 0 | 0 |
| Ref. Ex. 6 | BN + lactose + StMg | 0.16 mg/kg | 65 μm | 0.1 | 0 | 0 | 0 |

Note) BN represents buprenorphine hydrochloride. StMg represents magnesium stearate.

Example 5 and Comparative Examples 9 to 16

Diclofenac sodium (manufactured by Wako Pure Chemicals Industries, Ltd.), an analgesic, was sieved to an average particle size of 40, 15 or 4 μm. To 20 mg each of them, 180 mg of microcrystalline cellulose (manufactured by Asahi Chemical Industry, Co., Ltd.: Avicel PH101) was added and mixed in a mortar, to which 20 mg of hydroxypropyl cellulose (manufactured by Nippon Soda Co., Ltd.: HPC-H) and, as a lubricant, 0.16 mg of magnesium stearate was added. For comparison, 20 mg of sieved diclofenac sodium (manufactured by Wako Pure Chemicals Industries, Ltd.) was taken, to which 200 mg of hydroxypropyl cellulose (manufactured by Nippon Soda Co., Ltd.: HPC-H) and, as a lubricant, 0.16 mg of magnesium stearate were added and mixed in a glass bottle on a ball mill rotary stage to prepare powder compositions.

In these cases, there were used microcrystalline cellulose (manufactured by Asahi Chemical Industry, Co., Ltd.: Avicel PH101) in which 90% by weight or more of the particles had an average size of 63 to 150 μm, and hydroxypropyl cellulose (manufactured by Nippon Soda Co., Ltd.: HPC-H) in which 90% by weight or more of the particles had an average size of 10 to 100 μm.

Two mg of diclofenac sodium alone (Comparative Examples 9 to 11), 20 mg of a mixture of diclofenac sodium and microcrystalline cellulose (Example 5 and Comparative Examples 12 and 13), or 20 mg of a mixture of diclofenac sodium and hydroxypropyl cellulose (Comparative Examples 14 to 16) were each administered to the nasal cavity of Japanese white rabbits, weighing 2.5 to 3.0 kg, using a pulverizer (manufactured by Teijin Ltd.: PUVRIZER). After a certain period of time, blood was taken from the ear vein, and blood concentrations of diclofenac sodium were measured by the HPLC method. The AUC (the area under the blood concentration versus time curve) calculated from changes with time in blood concentrations is shown in Table 4.

When the particle size of diclofenac sodium is 10 μm or smaller and the mixed ratio by weight of the water-slightly soluble and water-absorbing base material CC to said gel-forming base material HPC is in the range of 99:1 to 65:35 (Example 5), higher maximum blood concentrations were observed than those observed when the particle size is greater than 10 μm (Comparative Examples 12 and 13), when the water-absorbing and gel-forming base material alone is used (Comparative Examples 14 to 16), and when there are no base materials (Comparative Examples 9 to 11), indicating that the composition of the present invention exhibits markedly improved absorbability and markedly enhanced maximum blood concentrations. It is also clear that the particle size hardly affects absorbability when the main drug alone is present.

TABLE 4

AUC calculated from changes with time in blood concentrations of diclofenac sodium after the administration of each composition (μg/ml × min)

|  | Composition given | CC | HPC | Particle size | AUC |
| --- | --- | --- | --- | --- | --- |
| Com. Ex. 9 | DF alone |  |  | 4 μm | 18.5 |
| Com. Ex. 10 | DF alone |  |  | 15 μm | 20.0 |
| Com. Ex. 11 | DF alone |  |  | 40 μm | 19.8 |
| Ex. 5 | DF, CC, HPC, StMg | 90 | 10 | 4 μm | 360.8 |
| Com. Ex. 12 | DF, CC, HPC, StMg | 90 | 10 | 15 μm | 164.8 |
| Com. Ex. 13 | DF, CC, HPC, StMg | 90 | 10 | 40 μm | 135.0 |
| Com. Ex. 14 | DF, HPC |  | 100 | 4 μm | 60.5 |
| Com. Ex. 15 | DF, HPC |  | 100 | 15 μm | 58.7 |
| Com. Ex. 16 | DF, HPC |  | 100 | 40 μm | 65.5 |

Note) DF represents diclofenac, CC represents microcrystalline cellulose, and HPC represents hydroxypropyl cellulose. In the table, numerical figures in CC and HPC represent weight ratios. StMg represents magnesium stearate.

Example 6 and Comparative Examples 17 to 19

Buprenorphine hydrochloride (manufactured by Macfarlane Smith, Great Britain, average particle size of 65 μm), an analgesic, was ground in an mortar to an average particle size of 5 μm. To 4 mg each of the non-ground drug (Comparative Example 17) and the ground drug (Example 6), 180 mg of microcrystalline cellulose (manufactured by Asahi Chemical Industry, Co., Ltd.: Avicel PH101) was added and mixed in a mortar. To the mixture, 20 mg of hydroxypropyl cellulose (manufactured by Nippon Soda Co., Ltd.: HPC-H) and, as a lubricant, 0.16 mg of magnesium stearate was added and mixed in a mortar to prepare powder compositions. For comparison, buprenorphine hydrochloride (manufactured by Macfarlane Smith, Great Britain, average particle size of 65 μm) was ground on a mortar to an average particle size of 5 μm. To 4 mg each of the non-ground drug (Comparative Example 18) and the ground drug (Comparative Example 19), 200 mg of styrene divinylbenzene copolymer resin (an average size of 40 μm) and, as a lubricant, 0.16 mg of magnesium stearate was added and mixed in a mortar to prepare powder compositions.

In these cases, there were used microcrystalline cellulose (manufactured by Asahi Chemical Industry, Co., Ltd.: Avicel PH101) in which 90% by weight or more of the particles was made to have an average size of 63 to 150 μm, and hydroxypropyl cellulose (manufactured by Nippon Soda Co., Ltd.: HPC-H) in which 90% by weight or more of the particles was made to have an average size of 10–100 μm.

These compositions were administered to the nasal cavity of Japanese white rabbits, weighing 2.5 to 3.0 kg, using a pulverizer (manufactured by Teijin Ltd.: PUVRIZER) at a dose of 8 mg/kg. After a certain period of time, blood was taken from the ear vein, and blood concentrations of buprenorphine hydrochloride were measured by the HPLC method. The result is shown in Table 5.

When the particle size of buprenorphine hydrochloride is 10 μm or smaller and the mixed ratio by weight of the water-slightly soluble and water-absorbing base material CC to said gel-forming base material HPC is in the range of 99:1 to 65:35 (Example 6), higher maximum blood concentrations were observed than those observed when the particle size is 65 μm (Comparative Example 17) and when the non-polar adsorptive resin styrene divinylbenzene copolymer was used as the base material (Comparative Examples 18 and 19), indicating that the composition of the present invention exhibits markedly improved absorbability and markedly enhanced maximum blood concentrations.

TABLE 5

Changes with time in blood concentrations of buprenorphine hydrochloride after the administration of each composition (ng/ml)

|  | CC | HPC | Particle size | 15 min | 30 min | 60 min | 90 min |
| --- | --- | --- | --- | --- | --- | --- | --- |
| Ex. 6 | 90 | 10 | 5 μm | 6.4 | 5.0 | 3.2 | 1.8 |
| Com. Ex. 17 | 90 | 10 | 65 μm | 0.5 | 1.0 | 0.4 | 0.2 |
| Com. Ex. 18 |  |  | 5 μm | 2.3 | 1.8 | 0.9 | 0.5 |
| Com. Ex. 19 |  |  | 65 μm | 0.2 | 0.6 | 0.3 | 0.2 |

Note) In the table, CC and HPC represent weight ratios.

When Example 6 (the particle size of the drug is 5 μm) and Comparative Example 17 (the particle size of the drug is 65 μm) are compared, it is clear that the absorbability of drugs is markedly enhanced when the two base materials of the present invention are combined at a certain ratio. In contrast, when Comparative Example 18 (the particle size of the drug is 5 μm) and Comparative Example 19 (the particle size of the drug is 65 μm) are compared, it is clear that the absorbability of drugs is not significantly enhanced when the two base materials of the present invention are not used. This demonstrates that in order to enhance the absorbability of drugs, it is necessary to satisfy the condition that the particle size of the drugs should be less than 10 μm and the condition that the two base materials of the present invention should be used in a certain ratio.

Example 7 and Comparative Example 20

To 200 mg of porcine insulin (manufactured by Sigma, USA, an average particle size of 2 μm), a peptide/protein drug, 1800 mg of microcrystalline cellulose (manufactured by Asahi Chemical Industry, Co., Ltd.: Avicel PH101) was added and mixed in a high speed mixer, and then 200 mg of hydroxypropyl cellulose (manufactured by Nippon Soda Co., Ltd.: HPC-H) and, as a lubricant, 1.6 mg of magnesium stearate were added and mixed in a cross rotary mixer to prepare a powder composition (Example 7). For comparison, to 200 mg of porcine insulin (manufactured by Mallinckrodt, USA, an average particle size of 2 $\mu$m), 2000 mg of a styrene divinylbenzene copolymer resin (an average particle size of 40 $\mu$m) was added and mixed in a high speed mixer, and then 1.6 mg of magnesium stearate was added to a lubricant and mixed in a cross rotary mixer to prepare a powder composition (Comparative Example 20).

In these cases, there were used microcrystalline cellulose (manufactured by Asahi Chemical Industry, Co., Ltd.: Avicel PH101) in which 90% by weight or more of the particles was made to have an average size of 63–150 $\mu$m, and hydroxypropyl cellulose (manufactured by Nippon Soda Co., Ltd.: HPC-H) in which 90% by weight or more of the particles was made to have an average size of 10–100 $\mu$m.

These compositions were administered to the nasal cavity of Japanese white rabbits, weighing 2.5–3.0 kg, at a dose of 8 mg/kg using a pulverizer (manufactured by Teijin Ltd.: PUVRIZER). After a certain period of time, blood was taken from the ear vein, and blood concentrations of insulin were measured by a commercially available kit for measuring blood concentrations of insulin. The result is shown in Table 6.

When the particle size of insulin is 10 $\mu$m or smaller and the mixed ratio by weight of the water-slightly soluble and water-absorbing base material CC to said gel-forming base material HPC is in the range of 99:1 to 65:35 (Example 7), higher maximum blood concentrations were observed than that observed when the non-polar adsorptive resin styrene divinylbenzene copolymer was used as a base material (Comparative Example 20), indicating that the composition of the present invention exhibits markedly improved absorbability and markedly enhanced maximum blood concentrations.

TABLE 6

Changes with time in blood concentrations of insulin after the administration of each composition (mU/ml)

| | Particle size | 15 min. | 30 min. | 60 min. | 90 min. |
|---|---|---|---|---|---|
| Ex. 7 | 2 $\mu$m | 2.4 | 1.7 | 1.2 | 0.4 |
| Com. Ex. 20 | 2 $\mu$m | 1.0 | 0.3 | 0.05 | 0.02 |

From the above results, it is clear that the use of drugs having a particle size of 10 $\mu$m does not naturally lead to enhanced absorbability, but that the enhanced absorbability observed when drugs having a particle size of 10 $\mu$m are used can be attained only by the combination of the water-slightly soluble and water-absorbing base material and the gel-forming base material of the present invention.

Examples 8 and 9, Comparative Examples 21 to 24 and Reference Example 7

Buprenorphine hydrochloride (manufactured by Macfarlane Smith, Great Britain, average particle size of 65 $\mu$m), an analgesic, was prepared as an aqueous solution and lyophilized. To 4 mg of this, 180 mg or 160 mg of microcrystalline cellulose (manufactured by Asahi Chemical Industry, Co., Ltd.: Avicel PH101) was added and mixed in a mortar. To the mixture, 20 mg or 40 mg of hydroxypropyl cellulose (manufactured by Nippon Soda Co., Ltd.: HPC-H) and, as a lubricant, 0.16 mg of magnesium stearate were added and mixed in a mortar to prepare powder compositions (Examples 8 and 9).

For comparison, buprenorphine hydrochloride (manufactured by Macfarlane Smith, Great Britain, average particle size of 65 $\mu$m) was prepared as an aqueous solution and lyophilized. To 4 mg of this, 110 mg or 80 mg of microcrystalline cellulose (manufactured by Asahi Chemical Industry, Co., Ltd.: Avicel PH101) was added and mixed in a mortar. To the mixture, 90 mg or 120 mg of hydroxypropyl cellulose (manufactured by Nippon Soda Co., Ltd.: HPC-H) and, as a lubricant, 0.16 mg of magnesium stearate were added and mixed in a mortar to prepare powder compositions (Comparative Examples 21 and 22).

Furthermore, for comparison, 4 mg of buprenorphine hydrochloride (manufactured by Macfarlane Smith, Great Britain, average particle size of 65 $\mu$m) was taken as it is, to which 180 mg or 160 mg of microcrystalline cellulose (manufactured by Asahi Chemical Industry, Co., Ltd.: Avicel PH101) was added and mixed in a mortar. To mixture, 20 mg or 40 mg of hydroxypropyl cellulose (manufactured by Nippon Soda Co., Ltd.: HPC-H) and, as a lubricant, 0.16 mg of magnesium stearate were added and mixed in a mortar to prepare powder compositions (Comparative Examples 23 and 24).

As a Reference Example, 4 mg of buprenorphine hydrochloride (manufactured by Macfarlane Smith, Great Britain, average particle size of 65 $\mu$m) and 180 mg of microcrystalline cellulose (manufactured by Asahi Chemical Industry, Co., Ltd.: Avicel PH101) were dissolved and suspended in 20 ml of purified water in a 50 ml beaker, and then lyophilized. To the lyophilized product, 20 mg of hydroxypropyl cellulose (manufactured by Nippon Soda Co., Ltd.: HPC-H) and, as a lubricant, 0.16 mg of magnesium stearate were added and mixed in a mortar to prepare a powder composition (Reference Example 7).

In these cases, there were used microcrystalline cellulose (manufactured by Asahi Chemical Industry, Co., Ltd.: Avicel PH101) in which 90% by weight or more of the particles had an average size of 63 to 150 $\mu$m, and hydroxypropyl cellulose (manufactured by Nippon Soda Co., Ltd.: HPC-H) in which 90% by weight or more of the particles had an average diameter of 10 to 100 $\mu$m.

These compositions were administered to the nasal cavity of Japanese white rabbits, weighing 2.5 to 3.0 kg, using a pulverizer (manufactured by Teijin Ltd.: PUVRIZER) at a dose of 8 mg/kg. After a certain period of time, blood was taken from the ear vein, and blood concentrations of buprenorphine hydrochloride were measured by the HPLC method. The result is shown in Table 7.

When buprenorphine hydrochloride is lyophilized or the mixed ratio by weight of the water-slightly soluble and water-absorbing base material CC to the gel-forming base material HPC is in the range of 99:1 to 65:35 (Examples 8 and 9), higher maximum blood concentrations were observed than those observed when the drug was not lyophilized (Comparative Examples 23 and 24), when the mixed ratio of the water-slightly soluble and water-absorbing base material CC to the gel-forming base material HPC is in the range of 55:45 or 40:60 (Comparative Examples 21 and 22), or when the drug was lyophilized together with the water-slightly soluble and water-absorbing base material CC (Reference Example 7), indicating that the composition of the present invention exhibits markedly improved absorbability and markedly enhanced maximum blood concentrations.

TABLE 7

Changes with time in blood concentrations of buprenorphine hydrochloride after the administration of each composition (ng/ml)

| | CC | HPC | lyophilization | 15 min. | 30 min. | 60 min. | 90 min. |
|---|---|---|---|---|---|---|---|
| Ex. 8 | 90 | 10 | Performed | 12.7 | 6.2 | 5.0 | 3.2 |
| Ex. 9 | 80 | 20 | Performed | 10.8 | 7.0 | 4.5 | 2.6 |
| Com. Ex. 21 | 55 | 45 | Performed | 1.5 | 1.2 | 1.0 | 0.6 |
| Com. Ex. 22 | 40 | 60 | Performed | 1.2 | 1.1 | 1.2 | 0.8 |
| Com. Ex. 23 | 90 | 10 | Not performed | 0.5 | 1.0 | 0.4 | 0.2 |
| Com. Ex. 24 | 80 | 20 | Not performed | 0.1 | 0.5 | 0.1 | 0 |
| Ref. Ex. 7 | 90 | 10 | Performed | 4.5 | 2.3 | 1.4 | 0.6 |

Note) In the table, CC and HPC represent weight ratios.

Examples 10 and 11, Comparative Examples 25 to 28 and Reference Example 8

Beclometasone propionate (manufactured by Sicor, USA, average particle size of 6 μm), a steroid drug, was prepared as an aqueous solution and lyophilized. To 5 mg of this, 160 mg or 140 mg of microcrystalline cellulose (manufactured by Asahi Chemical Industry, Co., Ltd.: Avicel PH101) was added and mixed in a high speed mixer. To the mixture, 40 mg or 60 mg of hydroxypropyl cellulose (manufactured by Nippon Soda Co., Ltd.: HPC-H) and, as a lubricant, 0.16 mg of magnesium stearate were added and mixed in a cross rotary mixer to prepare powder compositions (Examples 10 and 11).

For comparison, beclometasone propionate (manufactured by Sicor, USA, average particle size of 6 μm) was prepared as an aqueous solution and lyophilized. To 5 mg of this, 100 mg or 40 mg of microcrystalline cellulose (manufactured by Asahi Chemical Industry, Co., Ltd.: Avicel PH101) was added and mixed in a high speed mixer. To the mixture, 100 mg or 160 mg of hyroxypropyl cellulose (manufactured by Nippon Soda Co., Ltd.: HPC-H) and, as a lubricant, 0.16 mg of magnesium stearate were added and mixed in a cross rotary mixer to prepare powder compositions (Comparative Examples 25 and 26).

Furthermore, for comparison, 5 mg of beclometasone propionate (manufactured b Sicor, USA, average particle size of 6 μm) was taken as it is, to which 160 mg or 140 mg of microcrystalline cellulose (manufactured by Asahi Chemical Industry, Co., Ltd.: Avicel PH101) was added and mixed in a high speed mixer. To the mixture, 40 mg or 60 mg of hydroxypropyl cellulose (manufactured by Nippon Soda Co., Ltd.: HPC-H) and, as a lubricant, 0.16 mg of magnesium stearate were added and mixed in a cross rotary mixer to prepare powder compositions (Comparative Examples 27 and 28).

As an additional Reference Example, 5 mg of beclometasone propionate (manufactured by Sicor, USA, average particle size of 6 μm) and 160 mg of microcrystalline cellulose (manufactured by Asahi Chemical Industry, Co., Ltd.: Avicel PH101) were dissolved and suspended in 20 ml of purified water in a 50 ml beaker, and then was lyophilized. To the lyophilized product, 40 mg of hydroxypropyl cellulose (manufactured by Nippon Soda Co., Ltd.: HPC-H) and, as a lubricant, 0.16 mg of magnesium stearate were added and mixed in a high speed mixer to prepare a powder composition (Reference Example 8).

In these cases, there were used microcrystalline cellulose (manufactured by Asahi Chemical Industry, Co., Ltd.: Avicel PH101) in which 90% by weight or more of the particles was made to have an average size of 63 to 150 μm, and hydroxypropyl cellulose (manufactured by Nippon Soda Co., Ltd.: HPC-H) in which 90% by weight or more of the particles had an average size of 10 to 100 μm.

These compositions were administered to the nasal cavity of Japanese white rabbits, weighing 2.5 to 3.0 kg, using a pulverizer (manufactured by Teijin Ltd.: PUVRIZER) at a dose of 8 mg/kg. After a certain period of time, blood was taken from the ear vein, and blood concentrations of beclometasone propionate were measured by the RIA method. The result is shown in Table 8.

When beclometasone propionate is lyophilized or the mixed ratio by weight of the water-slightly soluble and water-absorbing base material CC to the gel-forming base material HPLC is in the range of 99:1 to 65:35 (Examples 10 and 11), higher maximum blood concentrations were observed than those observed when the drug was not lyophilized (Comparative Examples 27 and 28), when the mixed ratio of the water-slightly soluble and water-absorbing base material CC to the gel-forming base material HPC is in the range of 50:50 or 20:80 (Comparative Examples 25 and 26), or when the drug was lyophilized together with the water-slightly soluble and water-absorbing base material CC (Reference Example 8), indicating that the composition of the present invention exhibits markedly improved absorbability and markedly enhanced maximum blood concentrations.

TABLE 8

Changes with time in blood concentrations of beclometasone propionate after the administration of each composition (pg/ml)

| | CC | HPC | lyophilization | 15 min. | 30 min. | 60 min. | 90 min. |
|---|---|---|---|---|---|---|---|
| Ex. 10 | 80 | 20 | Performed | 40 | 34 | 24 | 8 |
| Ex. 11 | 70 | 30 | Performed | 36 | 28 | 20 | 12 |
| Com. Ex. 25 | 50 | 50 | Performed | 5 | 3 | 2 | 2 |
| Com. Ex. 26 | 20 | 80 | Performed | 3 | 4 | 2 | 2 |
| Com. Ex. 27 | 80 | 20 | Not performed | 25 | 20 | 12 | 8 |
| Com. Ex. 28 | 70 | 30 | Not performed | 20 | 22 | 18 | 12 |
| Ref. Ex. 8 | 80 | 20 | Performed | 28 | 16 | 10 | 3 |

Note) In the table, CC and HPC represent weight ratios.

Reference Example 9 and Examples 12 to 17

Buprenorphine hydrochloride (manufactured by Macfarlane Smith, Great Britain, average particle size of 65 μm), an analgesic, was prepared as an aqueous solution and lyophilized. In said lyophilization, the time of primary drying at 10° C. was 0, 2, 4, 6, 8, 10, or 20 hours. To 4 mg of these, 180 mg of microcrystalline cellulose (manufactured by Asahi Chemical Industry, Co., Ltd.: Avicel PH101) was added and mixed in a mortar. To the mixture, 20 mg of hyroxypropyl cellulose (manufactured by Nippon Soda Co., Ltd.: HPC-H) and, as a lubricant, 0.16 mg of magnesium stearate were added and mixed in a mortar to prepare powder compositions.

In these bases, there were used microcrystalline cellulose (manufactured by Asahi Chemical Industry, Co., Ltd.: Avicel PH101) in which 90% by weight or more of the particles had an average size of 63 to 150 μm, and hydroxypropyl cellulose (manufactured by Nippon Soda Co., Ltd.: HPC-H)

in which 90% by weight or more of the particles had an average size of 10 to 100 µm.

These compositions were administered to the nasal cavity of Japanese white rabbits, weighing 2.5 to 3.0 kg, using a pulverizer (manufactured by Teijin Ltd.: PUVRIZER) at a dose of 8 mg/kg. After a certain period of time, blood was taken from the ear vein, and blood concentrations of buprenorphine hydrochloride were measured by the HPLC method. The result is shown in Table 9.

It is clear that when buprenorphine hydrochloride is lyophilized or the mixed ratio by weight of the water-slightly soluble and water-absorbing base material CC to the gel-forming base material HPC is in the range of 99:1 to 65:35, the absorbability of drugs change depending on the time of primary drying at said lyophilization, and that the compositions of the present invention prepared with a primary drying time of 6–10 hours exhibit markedly improved absorbability and markedly enhanced maximum blood concentrations.

TABLE 9

Changes with time in blood concentrations of buprenorphine hydrochloride after the administration of each composition (ng/ml)

| | Primary drying time | 15 min | 30 min | 60 min | 90 min |
|---|---|---|---|---|---|
| Ref. Ex. 9 | 0 | 2.7 | 1.2 | 0.5 | 0.2 |
| Ex. 12 | 2 | 10.8 | 7.0 | 4.5 | 2.6 |
| Ex. 13 | 4 | 12.7 | 6.2 | 5.0 | 3.2 |
| Ex. 14 | 6 | 14.2 | 11.1 | 8.2 | 4.8 |
| Ex. 15 | 8 | 13.5 | 11.0 | 8.4 | 4.2 |
| Ex. 16 | 10 | 14.1 | 10.2 | 8.1 | 4.0 |
| Ex. 17 | 20 | 6.8 | 4.0 | 3.4 | 2.6 |

What is claimed is:

1. A power composition for nasal administration comprising (1) a drug having a particle size of 0.5 µm or more and less than 10 µm, (2) a water-absorbing and slightly-water soluble base material, and (3) a water-absorbing and gel-forming base material, wherein the mixed ratio by weight of said water-absorbing and slightly-water soluble base material to said water-absorbing and gel-forming base material is in the range of 99:1 to 65:35.

2. A powder composition for nasal administration comprising (1) a drug having a particle size of less than 10 µm, wherein the particle size of said drug is made less than 10 µm by pulverizing and sieving, (2) a water-absorbing and slightly-water soluble base material, and (3) a water-absorbing and gel-forming base material, wherein the mixed ratio by weight of said water-absorbing and slightly-water soluble base material to said water-absorbing and gel-forming base material is in the range of 99:1 to 65:35.

3. A powder composition for nasal administration comprising (1) a drug having a particle size of less than 10 µm, wherein the particle size of said drug is made less than 10 µm by spray drying, (2) a water-absorbing and slightly-water soluble base material, and (3) a water-absorbing and gel-forming base material, wherein the mixed ratio by weight of said water-absorbing and slightly-water soluble base material to said water-absorbing and gel-forming base material is in the range of 99:1 to 65:35.

4. A powder composition for nasal administration comprising (1) a drug having a particle size of less than 10 µm, wherein the particle size of said drug is made less than 10 µm by lyophilization, (2) a water-absorbing and slightly-water soluble base material, and (3) a water-absorbing and gel-forming base material, wherein the mixed ratio by weight of said water-absorbing and slightly-water soluble base material to said water-absorbing and gel-forming base material is in the range of 99:1 to 65:35.

5. The powder composition for nasal administration according to claim 2, wherein said water-absorbing and gel-forming base material is a cross-linked starch or a lower alkyl ether of cellulose.

6. The powder composition for nasal administration according to claim 3, wherein said water-absorbing and gel-forming base material is a cross-linked starch or a lower alkyl ether of cellulose.

7. The powder composition for nasal administration according to claim 4, wherein said water-absorbing and gel-forming base material is a cross-linked starch or a lower alkyl ether of cellulose.

8. The powder composition for nasal administration according to claim 5, wherein said lower alkyl ether of cellulose is one or more than one lower alkyl ether of cellulose selected from the group consisting of hydroxypropyl cellulose, hydroxypropyl ethyl cellulose, carboxymethyl cellulose, carboxymethyl cellulose sodium, and carboxymethyl cellulose calcium.

9. The powder composition for nasal administration according to claim 6, wherein said lower alkyl ether of cellulose is one or more than one lower alkyl ether of cellulose selected from the group consisting of hydroxypropyl cellulose, hydroxypropyl ethyl cellulose, carboxymethyl cellulose, carboxymethyl cellulose sodium, and carboxymethyl cellulose calcium.

10. The powder composition for nasal administration according to claim 7, wherein said lower alkyl ether of cellulose is one or ore than one lower alkyl ether of cellulose selected from the group consisting of hydroxypropyl cellulose, hydroxypropyl ethyl cellulose, carboxymethyl cellulose, carboxymethyl cellulose sodium, and carboxymethyl cellulose calcium.

11. The powder composition for nasal administration according to any one of claims 1, 2, 3 and 4, wherein said water-absorbing and slight-water soluble base material is one or more than one selected from the group consisting of crystalline cellulose, α-cellulose, dextran, chitin, and chitosan.

12. The powder composition for nasal administration according to claim 1, wherein said water-absorbing and gel-forming base material is a cross-linked starch or a lower alkyl ether or cellulose.

13. The powder composition for nasal administration according to claim 4, wherein said lower alkyl ether of cellulose is one or more than one lower alkyl ether of cellulose selected from the group consisting of hydroxypropyl cellulose, hydroxypropyl ethyl cellulose, carboxymethyl cellulose, carboxymethyl cellulose sodium, and carboxymethyl cellulose calcium.

14. A powder composition for nasal administration comprising (1) a lyophilized drug, (2) a slightly-water soluble and water-absorbing base material, and (3) a water-absorbing and gel-forming base material, wherein the mixed ratio by weight of said slightly-water soluble and water-absorbing base material to said water-absorbing and gel-forming base material is in the range of 99:1 to 65:35.

15. The powder composition for nasal administration according to claim 14 in which said lyophilized drug is a non-peptide/protein drug.

16. The powder composition for nasal administration according to claim 14 or 15 wherein said slightly-water soluble and water-absorbing base material is one or more than one selected from the group consisting of crystalline cellulose, α-cellulose, dextran, chitin, and chitosan.

17. The powder composition for nasal administration according to claim 14, wherein said water-absorbing and gel-forming base material is a cross-linked starch or a lower alkyl ether of cellulose.

18. The powder composition for nasal administration according to claim 11 wherein said lower alkyl ether of cellulose is one or more than one lower alkyl ether of cellulose selected from the group consisting of hydroxypropyl cellulose, hydroxypropyl methyl cellulose, carboxymethyl cellulose, carboxymethyl cellulose sodium, and carboxymethyl cellulose calcium.

* * * * *